United States Patent [19]
Arad et al.

[11] Patent Number: 5,643,585
[45] Date of Patent: Jul. 1, 1997

[54] COLORING MATERIALS

[75] Inventors: Shoshana Arad, Omer; Anina Yaron, Beer-Sheva; Ephraim Cohen, Lehavim, all of Israel

[73] Assignee: Ben-Gurion University of the Negev - Research and Development Authority, Beer-Sheva, Israel

[21] Appl. No.: 503,555

[22] Filed: Jul. 18, 1995

[30] Foreign Application Priority Data

Jul. 21, 1994 [IL] Israel .......................................... 110396

[51] Int. Cl.$^6$ ....................................................... A61K 7/00
[52] U.S. Cl. ............................................ 424/401; 424/489
[58] Field of Search ...................................... 424/401, 489

[56] References Cited

FOREIGN PATENT DOCUMENTS

| 1113318 | 2/1966 | European Pat. Off. . |
| 2 674126 | 9/1992 | France . |
| 1 113 318 | 6/1968 | United Kingdom . |

OTHER PUBLICATIONS

Patent abstract of Japan, vol. 013, No. 367 (C–626), Aug. 15, 1989; and JP–A–01 123 865, May 16, 1989.

Patent abstract of Japan, vol. 009 No. 196 (C–297), Aug. 13, 1985; and JP–A–60 064 906, Apr. 13, 1985.

Patent abstract of Japan, vol. 012 No. 353 (C–530), Sep. 21, 1988; and JP–A–63 109, 787 May 14, 1988.

Patent abstracts of Japan, vol. 013 No. 402 (C–633), Sep. 6, 1989; and JP–A–01 146 961, Jun. 8, 1989.

ERIMOCHIYOU "Production of Cosmetic Base" (see Abstract).

*Primary Examiner*—Thurman K. Page
*Assistant Examiner*—William Benston, Jr.
*Attorney, Agent, or Firm*—Kane, Dalsimer, Sullivan, Kurucz, Levy, Eisele and Richard, LLP

[57] ABSTRACT

A non-soluble particulate coloring material comprises dry ground red microalgae-derived material as the base coloring matter.

20 Claims, No Drawings

COLORING MATERIALS

THE FIELD OF THE INVENTION

The present invention relates to the preparation of natural coloring materials and to their use. More particularly, the invention relates to the use of red microalgae as coloring materials.

BACKGROUND OF THE INVENTION

It is known in the art to produce pigments from algae, and to extract such pigments from the algal body (cells), to produce soluble coloring materials. One instance of such a use is the production of carotenoids from algae such as Dunaliella, which are used in a variety of uses, and as coloring materials.

While green-yellow pigments (which may be obtained, e.g., from Dunaliella) are characterized by good solubility in organic solvents, the pigments extracted from red microalgae (phycobiliproteins) are soluble in water. Furthermore, phycobiliproteins are relatively expensive to produce, are sensitive to heat and light, and are stable only for relatively short periods of time.

SUMMARY OF THE INVENTION

It is an object of the present invention to provide coloring material which is highly stable for long periods of time. The coloring materials according to this invention are obtained from red microalgae.

It is another object of the invention to provide coloring materials having a wide range of colors and applications. Other objectives of the invention will become apparent as the description proceeds.

The red microalgae include about eight genera, the best known of which are Porphyridium, Rhodella and Rhodosorus. Morphologically, they are the simplest of all the red algae, and their reproduction is asexual. In most species the algal cells are brown as a result of their chlorophyll, carotenoids and phycobiliproteins contents. Some have different colors as a result of different ratios between phycoerythrins and phycocyanins. Many strains grow in fresh water, while others grow in seawater.

The cells of the red microalgae are encapsulated within a sulfated polysaccharide in the form of a gel. The capsules are thinnest during the logarithmic phase of growth and thickest during the stationary phase. It has been found that during the stationary growth phase the rate of polysaccharide production is higher than the rate of solubilization of the polysaccharide from the cell surface into the external medium. This process facilitates the creation of a capsule, and as a consequence cells reach their maximum size at the stationary phase of growth. It seems that the thickness of the capsule is influenced by three factors: the rate of polysaccharide production, the degree of polysaccharide solubility, and the cell surface area. During growth of Porphyridium in a liquid medium, the viscosity of the medium increases due to the release of polysaccharide from the cell surface.

The coloring material according to the invention comprises dry ground red microalgae as the base coloring matter. To this base coloring matter, of course, additional colors or additives can be added. Sometimes chlorophyll and carotenoids are first removed from the biomass by extraction. Preferably, the size of the particles of the powder obtained by the grinding of the algae is 50µ or less. While, as stated, a number of red microalgae exists, preferred genera are Porphyridium (e.g., Porphyridium sp. and *Porphyridium aerugineum*) and Rhodella (e.g., *Rhodella reticulata.*)

It should be emphasized that the coloring materials according to the invention are non-soluble, dispersible materials and in powder form. In comparison, prior art pigments obtained from red microalgae and other algae are soluble products. According to the invention, an extraction operation is carried out to remove undesirable materials (e.g., impurities or chlorophyll and salts which may adversely affect the final color of the product), but never to extract the desirable coloring material (phycobiliproteins), as is done in the known art. Furthermore, since many desirable properties of the coloring material of the invention derive from the fact that the pigments are contained within cells which are encapsulated with polysaccharides, it is clear that soluble pigments are entirely different products, with which the invention is not concerned. As stated, soluble pigments suffer from drawbacks, such as low light and shelf stability.

The coloring material prepared according to the invention results in a non-soluble powder having good workability, smoothing and lubricating feeling on the skin, and which can be applied, e.g., in cosmetic uses, as such, e.g., as a face makeup, or in lipstick or an eye shadow bases. The powder can be compressed, or used as such, as customary in this art, or can be provided with a carrier, such as a talc, kaolin, zinc stearate or hardened fats and waxes, or any other suitable carrier. Of course, other additives, such as fragrance materials, can also be added to the powder.

Furthermore, the coloring materials according to the invention not only are not suspect of causing allergic reactions, but are also edible and therefore can be used as coloring materials for food products. Accordingly, cosmetic or food preparations, employing as a coloring material ground red microalgae also form a part of the present invention.

Another advantage of the invention is that, as will be more fully explained hereinafter, it is possible to obtain a variety of colors and shades by varying growth and process conditions and using additives. Other means to control the final color are also available. For instance, extraction procedures alga age and growth conditions may affect the resulting color, the amount of phycobiliproteins in the cell influences the shade, and the base material in which the preparation is sometime incorporated (e.g., dry cake or wax-based cream) may substantially influence the final color obtained. This latter effect is due to the fact that the coloring material is provided in the form of fine particles. As will be appreciated by the skilled person, light diffraction is different in different media (e.g., in the presence of oily materials or in a compressed cake), which influences the color finally seen by the eye. Because of the aforesaid factors, a suprisingly large number of colors and shades can be obtained through the preparation of coloring matters from red microalgae, according to the invention.

As stated, among the advantages of the invention is the fact that, with the exception of a work-up, as will be described hereinafter, preparation of the material is thus directly from the algal body by a simple grinding Accordingly, the process for producing the coloring material is very simple, and the amount of lost material is relatively low.

Additionally, as stated above, the stability of the color is very important. Stability is obtained in the coloring material of the invention by the fact that the entire algal cell is employed, thus maintaining the encapsulation of the pigment by the sulfated polysaccharides which encapsulate the cells. These polysaccharides protect the pigment from deterioration, and are largely responsible for the improved stability of these pigments. In other words, the shelf life of the pigment which has been extracted from the cell of the red microalgae is substantially shorter than the shelf life of the very same pigment which has been kept within the cell. As stated, the smooth and lubricating feeling obtained with the coloring material according to the invention is an important feature in cosmetic preparations. The polysaccharides which envelop the coloring materials are largely responsible for this effect. As would be appreciated by the skilled person, it is surprising that it is possible to employ the cells of red microalgae as such, without extracting the pigment therefrom, and that the material obtained is usable without requiring transformation or particular and complicated procedures.

Also encompassed by the invention is a process for preparing a coloring material, which process comprises cultivating red microalgae to produce a biomass, and then carrying out, in any convenient order, the steps of:

a) extracting undesirable extractable materials from the algal body thereby removing them therefrom;

b) removing water from the algal body;

c) grinding the red microalgae, preferably to a particle size of 50µ or less.

If required, additional drying of the algal body can be effected before or after grinding. However, according to a preferred embodiment of the invention the extraction of undesirable materials is effected with a solvent which removes also water, and therefore water removal is automatically achieved during the extraction operation.

According to another preferred embodiment of the invention, the water removal operation can be carried out by freeze-drying, and furthermore the dried algae can be extracted prior to grinding with a volatile solvent, to remove pigments (chlorophylls and carotenoids) and impurities which are present within the algae. The solvent can be a suitable solvent which is not damaging to the cell, and which does not leave traces which are dangerous to health, and a preferred solvent is acetone.

It is also possible to effect the drying (e.g., the removal of water) and extraction of impurities in one step, by extracting the wet algae with an organic solvent, followed by vaporization of the solvent, this, as will be appreciated, will remove also water together with the impurities. The organic solvent is preferably selected from among acetone, alcohols and isopropanol.

As will be apparent to a skilled person, different algae can produce different colors and intensity of colors, under different growth conditions. In the red microalgae pigments known as phycobiliproteins are largely responsible for differences in final color. Phycobiliproteins are pigments, red and blue in color. They absorb light in the visible region of 450 to 650 nm. Phycoerythrin, which is the pigment present in the largest amount in certain red algae, is located at the periphery of the phycobilisomes. Phycocyanin is located in the phycobilisomes between phycoerythrin and allophycocyanin (or at the periphery if phycoerythrin is absent). The specific absorption spectra and specific fluorescence emissions at wavelength maxima of the phycobiliproteins are known [R. MacColl and D. Guard, Friars Eds., "Phycobiliproteins", CRC Press, Florida (1987)].

Growth conditions, e.g., light conditions, culture age and medium composition may affect both the content and the composition of the phycobiliproteins. Red algae grown under low light intensity have an enhanced concentration of phycolbiliproteins per biomass. Similarly, in the red microalgae phycobiliproteins content decreases with the removal of nitrogen and sulfate from the medium.

Accordingly, the invention also comprises a process for preparing a coloring material having a desired color, comprising:

a) selecting a red microalga;

b) growing the said microalga under conditions suitable for increasing or reducing the content of phycobiliproteins therein; and c) harvesting the algae and drying and grinding the same, to obtain a powder having the desired color.

It has further been found, and that is another object of the invention, that three important characteristics of the process, namely, the intensity of the color of the powder, the variety of the produced colors and the stability of the pigments, may be significantly improved by modifying the above-described methods by applying acidic conditions at the work-up stage of the algae. This procedure permits to obtain coloring materials from algae whose physiological conditions were inferior, and to produce more intense colors than can be obtained without it. According to this acidic procedure, the algae are cultured and harvested at two growth stages. To the wet precipitate, after centrifugation, acidified water (0.1 N HCl or $H_3PO_4$) is added, and then the algae are dispersed and centrifuged again, and the acidified water are washed out. The precipitate is then extracted with an organic solvent, dried and ground, as hereinbefore described, to obtain the desired powder. The improvement in the parameters reflecting the intensity of the colors, their variety and pigment's stability will be illustrated in the examples to follow.

DETAILED DESCRIPTION OF THE INVENTION

The following materials and methods were employed in preparing various coloring compositions:

Algae and their growing method

The following algae were employed in the examples:

Porphyridium sp. (UTEX 637—"Jones R.F. et al., Physiol. Plant. 16. 636–643 [1963]"), growing in artificial seawater, *Porphyridium aerugineum*, (110.79—U.S. Pat. No. 4,079,544), growing in fresh water, and *Rhodella reticulata* (UTEX LB 2320—"Schlosser. U. G., Ber Deutsche Bot. Ges. 95, 272 [1982]"), growing in brackish water. In all cases the algae were grown outdoors in polyethylene sleeves having a wall-thickness of 0.2 cm, diameter of 32 cm and medium volume of 25–30 liters. The biomass is mixed by air containing 2–3% $CO_2$ (Cohen E. and Arad (Malis) S., 1989, Biomass 18, 59–67).

Determination of powder colors

The color of the powders prepared according to the invention was determined by using a spectrocolorimeter which determines tristimulus values according to the CIELa*b* method and a Spectrosystem Applied Color Systems Inc. apparatus. The method determines the spectrum of the reflected light, and the values are dependent on the method in which the sample was prepared for analysis, the means used to hold the sample, the particle size and the formulation. The sample was introduced in a transparent plastic bag for testing the colors. Representative results are shown in Table I below:

TABLE I

Characterization of the color of nonsoluble pigment powders by reflectance spectrophotometry[a]

| Color | L | a* | b* |
| --- | --- | --- | --- |
| Dark pink | 48.9 | 14.4 | −1.5 |
| Light pink | 55.6 | 19.1 | −0.5 |
| Dark petrol blue | 52.0 | −4.9 | −8.2 |
| Turquoise | 53.8 | −10.3 | 1.2 |

[a]L-lightness, (+a) red, (−a) green, (+b) yellow, (−b) blue

EXAMPLE 1

Preparation of a Cosmetic Preparation in Cake Form

Algae powder was used without additives to prepare a cosmetic preparation. The powder after grinding and sieving was used as an eye shade. The powder was also caked without additives, by introducing the powder into an aluminum form and pressing it by hydraulic pressure at different pressures between 0.5 and 5 atmospheres. The pressure employed was determined by the hardness of the cake that it was desired to obtain.

EXAMPLE 2

Making of a Cosmetic Make-Up With A Carrier

A formulation is prepared to be "spreadable," by using a mixture of fats, oils and waxes, as follows:

53% jojoba oil, 17% solidified jojoba oil 17% beeswax, and 13% glycerol monostearate. The mixture is heated to 70°°C. to melt the solidified oils and waxes, and is then cooled to room temperature with stirring. The coloring powder is mixed with titanium oxide, talc and zinc stearate, and the wax is then added with thorough mixing.

EXAMPLE 3

Effect of Work-Up Procedure on the Color

In order to test the effect of the work-up procedure on the intensity of the colors obtained, different materials were employed. It should be noted that algae dried in a lyophilizer contain also additional foreign matters, such as chlorophyll and carotenoids, while during the extraction with acetone such pigments are removed from the product. The experiments were carried out with three different algae, and the results are shown in Table II below:

TABLE II

| Alga | Work-Up Procedure | Color | L | a* | b* |
| --- | --- | --- | --- | --- | --- |
| P. sp. | lyophilized | bluish pink | 52.6 | 12.2 | −2.9 |
| P. sp. | Acetone extraction | pink | 55.6 | 19.1 | −0.5 |
| P. aer | lyophilized | green-turquoise | 53.8 | −10.3 | 1.2 |
| P. aer | Acetone extraction | light blue | 57.2 | −5.2 | −2.2 |
| R. r. | lyophilized | black | nd | nd | nd |
| R. r. | Acetone extraction | light purple | 52.64 | 5.9 | −3.5 |

P = Porphyridium; R = Rhodella; nd = Not determined

EXAMPLE 4 pH Effect

The algae were cultured and harvested at two growth stages. To the wet precipitate, after centrifugation, acidified water (0.1 N HCl or $H_3PO_4$) was added, the algae were dispersed and centrifuged again, and the acidified water was washed out. The precipitate was extracted with acetone, dried and ground (as described above). The color of the powders of these pigments was determined by the method described hereinbefore, and is detailed in Tables IIIA and IIIB. An improved color variety is seen, reflected by the extended range of the L parameter (45<L<67). Low values of this parameter correspond to intense colors. When comparing Tables II and IIIA, it is evident that due to the acidic treatment it is possible to obtain colors which are characterized by values of the L parameter that are less then 50. Table IIIB shows coloring materials whose L parameter is above 60, which result from powders obtained from old cultures of algae, from which no colors can be obtained without the acid treatment.

TABLE III

| Alga | Work-Up Procedure | Color | L | a* | b* |
| --- | --- | --- | --- | --- | --- |
| | | Table IIIA | | | |
| P. sp. | acid and acetone | purplish red | 49.1 | 15.9 | −18.7 |
| R. r. | acid and acetone | deep bluish purple | 45.6 | 7.0 | −30.8 |
| | | Table IIIB | | | |
| P. sp. | acid and acetone | light purplish-red | 64.5 | 11.2 | −15.9 |
| P. aer | acid and acetone | light blue-turqoise | 66.0 | −16.9 | −11.5 |
| R. r. | acid and acetone | light bluish purple | 67.0 | 1.0 | −17.1 |

EXAMPLE 5

Red microalgal cells of Porphyridium sp. (UTEX 637) were grown in 5 polyethylene sleeves, 25 liters each in sea water medium, outdoors. After 5 days the culture was harvested in a CEPA semicontinuous centrifuge and the biomass was recovered. The wet biomass was homogenized with a Turax (Janke & Kunkel, Germany) homogenizer in 10 volumes of acetone. The cell suspension was lightly stirred overnight and then vacuum filtered to recover the wet powder. Five volumes of acetone were added, stirred overnight and refiltered. This stage was performed three more times. The wet powder was dried in vacuum oven with circulating air or on trays outdoor in the shade. The dried powder was ground in a laboratory mill (Janke & Kunkel, Germany), and sieved in a laboratory sieve shaker through a 300 mesh sieve (Fritsch, Germany).

The chemical composition of the powder was 42% protein, 32% polysaccharide and 5% ash. When preparing an eyeshade cream 5% of pigment powder is added.

The powder so obtained was fine and soft with a dark bluish red hue (L=52.9, a=15.7, b=−6.0).

EXAMPLE 6

Preparation of a Face Powder Cake

An oily mixture is prepared, containing 5 parts of glycerol monostearate and 10 parts of liquid jojoba wax. This mixture is heated to 75° C. (melt). To the melt cooled to 40° C. there are added the following mixed powders: 55 parts of algal pigment, 20 parts of talc, 10 parts of zinc stearate and, optionally, 10 parts of titanium oxide. Perfume is added as desired according to the specific use.

Algal pigment from Porphyridium sp. grown under full solar light for 10 days would give pink-beige powder suitable for face powder. Titanium dioxide addition add better surface cover and results in a more pinkish-blue color.

EXAMPLE 7

Preparation of an Eye Shadow Cream

A mixture including 13 parts of yellow beeswax, 13 parts hydrogenated jojoba wax and 10 parts glycerol monostearate in liquid jojoba wax, q.s., is melted by heating to 70° C. The homogeneous mixture so obtained is cooled to 40° C. and to it there are added 4 parts of zinc stearate, 10 parts of talc and 10 parts of algal pigment, together with jojoba oil. The total amount of jojoba oil added is 40 parts. Perfume, q.s., is also added.

In an alternative formula, 15 parts of titanium oxide are added to the melt, and 10 parts of a 70% bismuth oxychloride in mineral oil is mixed last.

*Porphyridium aeruginuem* gives a torquoise color addition of titanium oxide yields a product having a pastel color of bluish turquoise.

*Porphyridium aeruginuem* acetone powder will dye petrol blue, and with titanium dioxide it will dye light blue.

EXAMPLE 8

Allergenic Test of Algal Powder Pigments

Algal powder pigments of the algae P. sp. and P. aer were prepared as in Example 4. A 10% powder dispersion in 50% glycerol was prepared. Patients visiting at the allergy clinic were tested by the Prick test for reaction to the pigments. Two controls were used: a negative control—saline solution—and a positive control—hystamine in saline. The reaction of six patients was tested. The pigments did not cause any allergic reaction in any of the patients. Water-soluble phycobiliproteins, extracted from red microalgae, caused reaction in some patients.

EXAMPLE 9

Preparation of Colored Icing

On a double steamer, beat egg whites, add slowly sugar powder (100 g per egg) and continue beating until stiff. Cool to about 50° C. and mix in 0.5–2.0% color powder. Add vanilla flavor. The P. sp. powder will give a pink-lilac color; P. aer, a light blue.

EXAMPLE 10

The effect of growth conditions on pigment intensity and hue values

The red microalga *P. aerugineum* was cultured outdoors and prepared as in Example 4. 100% light intensity at noontime outdoors was 1500–2000 $\mu E\ m^{-2} s^{-1}$.

TABLE IV

| Light intensity | Days of | Cell density | Color Parameters | | |
|---|---|---|---|---|---|
| ($\mu E\ m^{-2}\ s^{-1}$) | Growth | (cells × $10^6$/ml) | L | a* | b* |
| 100% | 3 | 15 | 55.0 | −5.2 | −8.6 |
| at noon | 6 | 17 | 57.2 | −5.2 | −2.2 |
| 50% | 3 | 11 | 52.0 | −4.9 | −8.2 |

TABLE IV-continued

| Light intensity | Days of | Cell density | Color Parameters | | |
|---|---|---|---|---|---|
| ($\mu E\ m^{-2}\ s^{-1}$) | Growth | (cells × $10^6$/ml) | L | a* | b* |
| (by artificial | 6 | 17 | 49.7 | −4.6 | −8.8 |
| shading) | 9 | 17 | 62.4 | −7.9 | −9.0 |

EXAMPLE 11

Effect of Formulation On Pigment Intensity and Hue Value

The pigment sample was prepared from under high light intensity, prepared as in Example 4.

TABLE V

| Components in Formulation (Parts) | | | | | | Color Parameters | | |
|---|---|---|---|---|---|---|---|---|
| Algal color | I.P.P. | Talc | TiO: | GMS | ZnSt | L | a* | b* |
| 60 | 5 | 20 | — | 5 | 10 | 43.9 | 17.7 | 5.5 |
| 60 | 10 | 20 | — | 5 | 10 | 48.1 | 17.9 | 5.5 |

IPP - isopropyl palmitate
GMS - glycerol monostearate
ZnSt - zinc stearate

The mixture of oils was dissolved at 70° C. and cooled to room temperature, and talc, ZnSt and $TiO_2$ were added with homogenizationin a mortar.

TABLE VI

| Components in Formulation (Parts) | | | | | Color Parameters | | |
|---|---|---|---|---|---|---|---|
| Algal color | $TiO_2$ | I.P.P. | GMS | ZnSt | L | a* | b* |
| 60 | — | 10 | 5 | 10 | 43.9 | 17.7 | 6.2 |
| 60 | 10 | 10 | 5 | 10 | 62.0 | 14.9 | −2.4 |

EXAMPLE 12

Composition of the Dry Powder of Pigment Samples

The preparation is as in Example 4. 100% of light intensity was 800–1200 $\mu E\ m^{-2}s^{-1}$.

TABLE VII

| | | Light | Pigment Composition | | |
|---|---|---|---|---|---|
| Micro-algal species | Days of Growth | intensity (solar light outdoors) (%) | protein (%) | poly-saccharide (%) | ash (%) |
| P. sp. | 7 | 50* | 42.2 | 32.0 | 4.6 |
| aer | 7 | 100 | 29.9 | 59.1 | |
| 2.4 | | | | | |
| P. aer | 14 | 50* | 43.5 | 42.3 | 3.1 |
| r. | 7 | 100 | 32.0 | 52.0 | 7.6 |

*Obtained by artificial shading

EXAMPLE 13

Stability of the Powder to Heat and Light

Samples of powders prepared according to Example 5 were subjected to heat and light treatment as detailed in Table VIII. The visible absorption of dispersion of the powder in glycerol was determined before and after exposure to heat. The absorption of the treated dispersions was lower after treatment. The absorption before treatment is taken as 100%.

TABLE VIII

| Treatment applied | Visible Absorption retained post-treatment (%) | | |
|---|---|---|---|
| | P. sp. | P. aer | R. r |
| Heat* | | | |
| 40° C., 60 minutes | 100 | 56 | 78 |
| 60° C., 30 minutes | 100 | 43 | N.D. |
| 80° C., 5 minutes | 66 | 35 | N.D |
| 100° C., 5 minutes | 0–10 | 0 | N.D |
| light** | | | |
| 1 day direct*** sunlight | 100 | 100 | 100 |

*0.1% pigment dispersion in glycerol
**pigment dispersion - either 0.1% in glycerol or 1% in hardened fat.
***= (500–1000 µE m$^{-2}$ sec$^{-1}$)
N.D = Not determined

EXAMPLE 14 pH Effect on the Stability of the powder

The powders prepared according to Example 4, were subjected to heat in a manner similar to that of Example 13. The mean particle diameter of the powder was 10 µm. The results are given in Table IX. Again, the absorption before the treatment is taken as 100%.

TABLE IX

| Treatment applied | Visible Absorption retained post-treatment (%) | |
|---|---|---|
| | P. sp. | R. r |
| Heat* | | |
| 80° C., 5 minutes | 100 | 100 |
| 100° C., 5 minutes | 23 | 70 |

*0.1% pigment dispersion in glycerol

All the above discussion and examples have been given for the purpose of illustration, and are not intended to constitute a limitation of the invention. Many different procedures, growing conditions, drying methods, materials and apparatus can be used, as well as different products, preparations and formulations based on or including the colors of the invention can be provided, without exceeding the scope of the invention.

We claim:

1. A non-soluble particulate coloring material comprising dry ground red microalgae-derived material as the base coloring matter.

2. A coloring material according to claim 1, in the form of a powder having a mean particle diameter of 50 µm or less.

3. A coloring material according to claim 1, wherein the red microalga is selected from the genus Porphyridium or Rhodella.

4. A cosmetic preparation consisting essentially of a powder as claimed in claim 2, optionally in compressed form, alone or together with cosmetically acceptable additives and/or carriers.

5. A cosmetic preparation containing as the coloring agent the material of claim 1.

6. A food preparation containing as the coloring agent the material of claim 1.

7. A process for preparing a coloring material, comprising cultivating a red microalgae to produce a biomass, and then carrying out, in any convenient order, the steps of:

a) extracting undesirable extractable materials from the algal body;

b) removing water from the algal body;

c) grinding the red microalgae, preferably to a particle size of 50 µm or less.

8. A process according to claim 7, wherein water removal is effected by freeze-drying.

9. A process according to claim 7, wherein the dried algae are extracted prior to grinding with a volatile organic solvent, to remove undesired pigments such as chlorophyll and carotenoids, and impurities.

10. A process according to claim 9, wherein the organic solvent is acetone.

11. A process according to claim 7, wherein water removal is effected by extracting the wet algae with a polar solvent, followed by vaporization of the solvent.

12. A process according to claim 11, wherein the solvent is selected from acetone, alcohols and isopropanol.

13. A process for preparing a coloring material having a desired color, comprising:

a) selecting a red microalga;

b) growing the red microalga under conditions suitable for increasing or reducing the content of phycobiliprotein therein; and c) harvesting the algae, removing water therefrom and grinding the same, to obtain a powder having the desired color.

14. A process according to claim 13, further comprising lowering the pH of the biomas after harvest.

15. A process according to claim 14, wherein the pH is lowered by adding an acid.

16. A process according to claim 15, wherein the acid is HCl or $H_3PO_4$.

17. A method for increasing the stability of coloring materials as claimed in claim 1 comprising treating the algal raw material with an acid.

18. A method for improving the color intensity of coloring materials as claimed in claim 1 comprising treating the algal raw material with an acid.

19. A colored product containing as a coloring material a material according to any one of claim 1.

20. A coloring material, whenever prepared by the process of any one of claim 7.

* * * * *